United States Patent

Osipow et al.

[11] Patent Number: 5,433,943
[45] Date of Patent: Jul. 18, 1995

[54] DEODORANT AND/OR ANTIPERSPIRANT COMPOSITIONS

[76] Inventors: Lloyd I. Osipow, 9875 Harbour Lake Cir., Boynton Beach, Fla. 33437; Dorothea C. Marra, 107 Fernwood Rd., Summit, N.J. 07901; J. George Spitzer, 184 Bradley Pl., Palm Beach, Fla. 33480

[21] Appl. No.: 994,001

[22] Filed: Dec. 21, 1992

[51] Int. Cl.⁶ ............................ A61K 7/32; A61K 7/38
[52] U.S. Cl. ........................................ 424/65; 424/47; 514/774
[58] Field of Search .................... 424/65, 47; 514/774

[56] References Cited

U.S. PATENT DOCUMENTS

| | | | |
|---|---|---|---|
| 2,704,269 | 3/1955 | Tice | 514/774 |
| 4,537,782 | 8/1985 | Millet et al. | 514/78 |
| 4,839,158 | 6/1989 | Michael | 514/774 |
| 4,952,560 | 8/1990 | Kigasawa et al. | 514/774 |
| 5,244,652 | 9/1993 | Michaels | 514/774 |
| 5,271,934 | 12/1993 | Goldberg et al. | 424/66 |

FOREIGN PATENT DOCUMENTS 1485373 9/1977 United Kingdom .

OTHER PUBLICATIONS

The Principles and Practice of Modern Cosmetics, 1963, vol. 2, Harry, pp. 200–202.

*Primary Examiner*—C. Warren Ivy
*Assistant Examiner*—D. Margaret M. Mach
*Attorney, Agent, or Firm*—Morgan & Finnegan

[57] ABSTRACT

Antiperspirant and deodorant or deodorant compositions with enhanced water absorbency are obtained by including in the compositions gelatin along with means for raising its sol-gel transition temperature.

10 Claims, No Drawings

DEODORANT AND/OR ANTIPERSPIRANT COMPOSITIONS

BACKGROUND OF THE INVENTION

This invention is concerned with compositions that are applied to the axillae to deodorize and help keep the underarms dry. Conventional products that perform both functions are termed antiperspirants and employ astringents such as aluminum chlorhydrate or zirconium oxychloride aluminum hydroxychloride complex. They are believed to inhibit the production of perspiration by the sweat glands.

The compositions of this invention employ moisture absorbent materials to achieve at least part of the dryness effect. These materials are not drugs and do not affect the normal functioning of the sweat glands.

Moisture absorbent materials have been used in the past to help keep the underarms dry. Particularly noteworthy are GB 1,482,756 and U.S. Pat. No. 4,508,705. These prior art materials are water insoluble and absorb water to form non-tacky gels. Chemically, these materials are similar. They are anionic polyelectrolytes that have been cross-linked covalently or with metal cations having a valence of at least two. The exception noted are carboxypolymethylenes of GB 1,482,756. These are very high molecular weight anionic polyelectrolytes that have not been cross-linked.

In U.S. Pat. No. 4,659,564 it is mentioned that water absorbents of the prior art tend to suffer a reduction in their water absorbing capacity in the presence of electrolytes, including the ionic species present in sweat. Antiperspirant salts such as those based on aluminum and zirconium have a particularly strong adverse affect on water absorbents. U.S. Pat. No. 4,659,564 is concerned with the synthesis of new water absorbents that are resistant to such salts. In the example given, it is shown that a typical water absorbent, water-insoluble cross-linked sodium carboxymethyl cellulose, will lose 97% of its water-absorbency in the presence of aluminum zirconium hydroxychloride glycine complex, while their new synthetic polymer will only lose 57% of its water absorbency.

Most of the water absorbent materials of the prior art are synthetic polymers that have been prepared using reactive chemicals. The compositions are intended to be applied daily and kept on the skin 24 hours each day. Consequently, it is essential that these synthetic polymers be thoroughly purified to remove all traces of reactive chemicals. It is now recognized that traces of reactive chemicals can be quite insidious, taking years before the toxic effect is observed.

The cross-linked alginates and carragheenates of the prior art are natural materials that are recognized to be non-toxic. However, they lack heat stability. When compositions containing these polymers are maintained at 60° to 79° C. for many hours, as required for the manufacture of underarm sticks they discolor and suffer a loss of water-absorbing capacity.

OBJECTS OF THIS INVENTION

An object of this invention is to provide a cosmetic composition for application to the axillae that provides odor protection and helps to keep the underarms dry. Another object is to provide an underarm deodorant composition containing an effective amount of a water absorbent that is a natural material and is generally recognized as safe, and that is stable under normal processing conditions. Another object is to provide an underarm deodorant composition that, when applied to the axillae, does not become tacky in the presence of perspiration. An additional object is to provide a water-absorbent that can be used with astringent antiperspirant salts, such as aluminum and zirconium salts, without substantial loss of water absorbency.

DESCRIPTION OF THE INVENTION

It has long been recognized that for a material to function as a useful water-absorbent in an underarm antiperspirant and deodorant or deodorant composition it may be a polymeric material that is capable of absorbing water, while being essentially completely insoluble in water. Polymers that were soluble in water invariably went through a tack stage during absorption or evaporation, and the user would find this unpleasant. Further, the tacky polymer could even cause the hair in the axillae to stick together.

The practical way to obtain a water-insoluble water-absorbent was to convert a water-soluble polymer to an insoluble one by cross-linking it covalently or through use of a metal cation with a valence of at least two, and this has been the common practice of the prior art.

It has now been found that a grade of gelatin capable of going through a tack stage during absorption and/or evaporation of water can be converted from a tacky grade to a non tacky form with an increased capacity to absorb water by combining therewith a sufficient amount of electrolyte, having at least one ion with a value of three or more, to raise the sol-gel transition temperature of the gelatin by at least two degrees centigrade, and thereby convert the tacky grade of gelatin to a non-tacky form with an increased capacity to absorb water. Such a gelatin material is a water-soluble amphoteric polymer can be a particularly useful water-absorbent in antiperspirant and deodorant or deodorant compositions. The presence of these electrolytes with the gelatin largely or completely eliminates the normal tacky characteristic of the normally tacky grade of gelatin, even when the gelatin-electrolyte combination is present with water in the form of a sol.

A further effect of these electrolytes is that they raise the water absorbing capacity of deposits of gelatin-containing deodorant and/or antiperspirant compositions.

The fact that the electrolytes raise the sol-gel transition temperature of gelatin indicates possible interaction between the electrolyte and the gelatin. Such interaction may be very weak or it could be quite strong. Thus, increases in the transition temperature from as little as 2° C. to well over 30° C. have been observed. Surprisingly, even with a 2° C. increase, tackiness is essentially eliminated and water absorption is increased by about 50%. While the present invention is not limited to any theory of action there appears to be an interaction that is quite different from cross-linking of the prior art, since it does not result in insolubilizing the polymer, but merely raises the sol-gel transition temperature.

The electrolytes that are effective with gelatin are not readily characterized. Thus, for example, type A gelatin has an isoelectric zone between about pH 7 and 9, while that of type B is between pH 4.8 and 5.0. Sodium citrate at pH 6.6–6.8 is effective with both gelatin types. Type A gelatin carries a positive charge at this pH and one might expect interaction with the multivalent citrate anion while interaction with type B gelatin is less expected since it carries a negative charge at this pH.

With tetrasodium ethylenediamine tetra acetate, with a tetravalent anion, at pH 9.5 both types of gelatin carry a negative charge, yet there is an elevation in the sol-gel transition temperature.

Aluminum salts are particularly effective in raising the sol-gel transition temperature. Aluminum salts with complex, multivalent anions are more effective than aluminum chloride with its monovalent anion. At the pH values of solutions containing these salts, both types of gelatin carry a positive charge. Table 1 shows the transition temperatures of gelatin solutions containing various electrolytes.

In the practice of this invention with non-aerosol composition such as sticks and lotions, gelatin should be used in an amount of about 5 to 25% by weight based on the weight of the composition. The electrolyte should contain one or more ions with a valence of at least three and should be present in an amount sufficient to raise the sol-gel transition temperature of the gelatin by at least two degrees centigrade. The amount of electrolyte used should be about 1 to about 25% by weight, based on the weight of the composition.

Aerosol compositions contain much lower concentrations of active ingredients, and in such compositions gelatin should be used in an amount of about 1 to about 10% by weight, and the electrolyte about 0.2 to about 10% by weight, based on the total weight of the composition.

The liquid vehicle that is used as a carrier for the deodorant and/or antiperspirant compositions of this invention should be predominantly volatile and water-insoluble. It should be essentially anhydrous, containing no more than about 5% moisture in excess of that normally present in the other components of the composition. Antiperspirant salts and other electrolytes generally contain appreciable amounts of water of hydration, and gelatin will generally contain 9 to 12% water.

The use of liquid vehicles in antiperspirant and deodorant or lo deodorant compositions is well-known in the art. Most commonly, volatile cyclic silicones are used in essentially anhydrous, non-aerosol compositions. They may be represented by the formula—$(R_2SiO)_n$— where R is $C_1$–$C_4$ alkyl, n is 3 to 10 and the unsatisfied bonds on the oxygen and silicon atoms at the end of the chain are joined to one another to form a cyclic structure. Slowly volatile esters, such as diisopropyl succinate or diisopropyl adipate, may be used alone or in combination with the volatile silicones. Smaller amounts of non-volatile liquids and greases may also be included in the compositions. These act as emollients and they also help to bind the deposit to the skin after the volatile component has evaporated. Examples include non-volatile polydimethyl siloxanes, isopropyl myristate, lanolin and petrolatum.

Aerosols most commonly employ n-butane, isobutane and propane, in various proportions, as the volatile liquid vehicle. The non-volatile liquid component is commonly a fatty ester emollient such as isopropyl myristate and butyl stearate.

Additional components well known in the art may be incorporated in the antiperspirant and deodorant or deodorant compositions of this invention. Sticks are generally solidified with cetyl and/or stearyl alcohol, often in combination with other waxes, such as hydrogenated castor oil, glyceryl tribehenate, and paraffin. Lotions and creams may use lesser amounts of these waxes to thicken and suspend dispersed solids. More commonly, hydrophobic clays and colloidal silicas are used for this purpose. Other find-particle solids, such as talcs, calcium carbonate and magnesium stearate may also be used in these products to impart body, or give a dry feeling more quickly after application. Deodorant compositions may contain a low concentration of an astringent salt or they may contain such deodorant ingredients as sodium bicarbonate, zinc oxide, zinc phenolsulfonate, magnesium carbonate and various organic antimicrobial agents, such as benzyl alcohol, methylbenzethonium chloride and triclosan. Astringent salts used in antiperspirant and deodorant compositions include aluminum chlorhydrate, aluminum zirconium hydroxychloride glycine complex and aluminum zirconium chlorhydrate.

To obtain effective perspiration inhibition with non-aerosol compositions, it is necessary to use more than 5% by weight based on the total weight of the composition of the astringent salt, and generally from about 10 to 25% by weight is required. With aerosol compositions only about 2 to 5% by weight of the astringent salt is required for effective perspiration inhibition.

With respect to any dispersed solid particles (e.g. gelatin particles, electrolyte particles, astringent salt particles) used in this invention, the particle size should generally be below 150 microns and preferably below 45 microns.

Table 2 shows complete deodorant and/or antiperspirant compositions and the effect of gelatin as well as gelatin plus electrolyte on water absorption of the dry composition. It can be seen that 8% gelatin doubled the water absorption of the composition without polymer. When sodium citrate or disodium ethylenediamine tetra acetate was added, water absorption increased. With 15% gelatin, aluminum chlorhydrate and aluminum zirconium hydroxychloride glycine complex gave a 7 or 8-fold increase in water absorption (see examples).

The water absorption values were determined by first crumbling an underarm stick and drying it at about 50° C. to constant weight. The dry solids were then powered. Increments of water were then added to 10 gram sample and worked with a spatula until a further addition of water could not be absorbed or the mixture became very fluid.

In the examples that follow some of the examples contain ingredients commonly known as antiperspirant which are astringent salts that reduce the flow of perspiration and also function as deodorants while other examples contain deodorant ingredients which do not reduce the flow of perspiration. In the antiperspirant and deodorant or deodorant stick examples that follow, the wax blend was first prepared by melting the waxes together and mixing until homogeneous. The wax blend was combined with diisopropyl adipate, polydimethylsiloxane and benzyl alcohol and heated to about 80° C. to remelt the wax blend. After cooling to 70° C., the polydimethylcyclosiloxane and fragrance were mixed in, followed by the powders. After thorough mixing, and while continuing to mix, the molten composition was poured into chilled containers. The containers were kept cold until the sticks had set.

The lotion examples were prepared by combining hydrogenated castor oil with polydimethyl siloxane and diisopropyl adipate and heating to dissolve the wax. The polydimethylcyclosiloxane was added to the hot solution with mixing. After cooling to 45°–50° C., the powders, benzyl alcohol and fragrance were mixed in and the compositions were packaged.

In the examples:

DC 245 Fluid is polydimethylcyclosiloxane, 95% $D_5$ sold by the Dow Corning Corporation.

DC 225 Fluid is polydimethylsiloxane, 10 cs at 25° C. sold by the Dow Corning Corporation.

Rezal 36 GP SUF is aluminum zirconium hydroxychloride glycine complex, extra fine grade sold by Reheis Inc.

Micro Dry Ultra Fine is aluminum chlorhydrate, extra fine grade sold by Reheis Inc.

TABLE 1

| | \multicolumn{11}{c}{PARTS BY WEIGHT} | | | | | | | | | | |
|---|---|---|---|---|---|---|---|---|---|---|---|
| | A | B | C | D | E | F | G | H | I | J | K | L |
| Gelatin, type A | 7 | 7 | 7 | 7 | 7 | 7 | 7 | 7 | — | — | — | — |
| Water | 24 | 23 | 30 | 44 | 23 | 30 | 24 | 24 | 24 | 23 | 30 | 24 |
| Rezal 36GP[1] | — | 0.7 | 0.7 | — | — | — | — | — | — | 0.7 | 0.7 | — |
| Micro Dry[2] | — | — | — | 0.7 | — | — | — | — | — | — | — | — |
| Aluminum chloride | — | — | — | — | 0.7 | 0.7 | — | — | — | — | — | — |
| Sodium citrate | — | — | — | — | — | — | 3.5 | — | — | — | 3.5 | — |
| Versene[3] | — | — | — | — | — | — | — | 3.5 | — | — | — | — |
| Gelatin, type B | — | — | — | — | — | — | — | — | 7 | 7 | 7 | 7 |
| Sol Gel °C. | — | 52 | 49 | 67 | 40 | 35 | — | — | — | 42 | 38 | — |
| Gel Sol °C. | 32 | — | — | — | — | — | 36 | 34 | 34 | — | — | 39 |

[1]Aluminum zirconium hydroxychloride glycine complex sold by Reheis Inc.
[2]Aluminum chlorhydrate sold by Reheis Inc.
[3]Tetrasodium ethylenediamine tetra acetate sold by Dow Chemical Corp.

TABLE 2

| | \multicolumn{7}{c}{PARTS BY WEIGHT} | | | | | | |
|---|---|---|---|---|---|---|---|
| | A | B | C | D | E | F | G |
| DC 245 Fluid[1] | 43 | 44 | 43 | 54 | 43 | 42 | 43 |
| Ceraphyl 230[2] | 4 | 4 | 4 | 4 | 4 | 4 | 4 |
| DC Silicone 225[3] | 4 | 4 | 4 | 4 | 4 | 4 | 4 |
| Wax Blend[4] | 22 | 22 | 22 | 25 | 22 | 27 | 22 |
| Benzyl alcohol | 0.5 | 0.5 | 0.5 | 0.5 | 0.5 | 0.5 | 0.5 |
| Fragrance | 0.5 | 0.5 | 0.5 | 0.5 | 0.5 | 0.5 | 0.5 |
| Sodium Bicarbonate | 8 | 8 | — | — | — | — | — |
| Calcium Carbonate | 10 | 10 | 10 | — | — | — | — |
| Kaolin | — | — | — | — | — | 10 | — |
| Gelatin, type A | — | 8 | 8 | 8 | — | 8 | 8 |
| Rezal 36GP[5] | — | — | — | — | 15 | 2 | 15 |
| Versene[6] | — | — | 4 | — | — | — | — |
| Sodium citrate | — | — | — | 4 | — | — | — |
| Water absorption, g/g[7] | 0.5 | 0.9 | 1.4 | 1.4 | 0.7 | 2.2 | 2.3 |
| Water absorption, g/g gelatin | — | 6.0 | 8.8 | 7.4 | — | 14.3 | 14.4 |

[1]Polydimethylcyclosiloxane, 95% $D_5$ sold by Dow Corning Corp.
[2]Diisopropyl adipate sold by Van Dyke Corporation.
[3]Polydimethylsiloxane, 10 cs at 25° C. sold by Dow Corning Corporation.
[4]Same as in Example 1.
[5]Aluminum zirconium hydroxychloride glycine complex sold by Reheis Inc.
[6]Tetrasodium ethylenediamine tetra acetate sold by Dow Chemical Corporation.
[7]Grams water absorbed for gram of dry weight of composition.

EXAMPLE 1

| Deodorant Stick Composition | |
|---|---|
| | Parts by Weight |
| Wax Blend | |
| Stearyl alcohol | 7.3 |
| Cetyl alcohol | 6.9 |
| Hydrogenated coconut oil | 3.5 |
| Paraffin wax (140/145) | 6.9 |
| Hydrogenated castor oil | 9.0 |
| | 99.6 |
| Complete Composition | |
| DC 245 Fluid | 43.0 |
| Diisopropyl Adipate | 2.0 |
| DC 225 Fluid | 6.0 |
| Calcium Carbonate (extra fine) | 5.0 |
| Gelatin, under 45 microns | 12.0 |
| Sodium Citrate, under 45 microns | 6.0 |
| Wax blend | 25.0 |
| Benzyl Alcohol | 1.0 |
| Fragrance | 0.5 |
| | 100.5 |

After solvent evaporation, the powdered composition absorbed 1.5g per gram of dry solids, corresponding to 6.8g water per gram of gelatin.

EXAMPLES 2 AND 3

| Antiperspirant Stick Compositions | | |
|---|---|---|
| | \multicolumn{2}{c}{Parts by Weight Example} | |
| | 2 | 3 |
| DC245 Fluid | 37.0 | 37.0 |
| Diisopropyl Adipate | 2.0 | 2.0 |
| DC 225 Fluid | 6.0 | 6.0 |
| Rezal 36 GP SUF | 15.0 | — |
| Micro Dry, (Ultra Fine) | — | 15.0 |
| Gelatin, under 45 microns | 15.0 | 15.0 |
| Wax Blend* | 25.0 | 25.0 |
| Benzyl alcohol | 0.5 | 0.5 |
| Fragrance | 0.5 | 0.5 |

*Same as in Example 1

After evaporating off the solvent, the powdered dry compositions of Examples 2 and 3 each absorbed 4.5 grams of water per gram of solids, corresponding to 19 grams of water per gram of gelatin.

EXAMPLE 4

| Lotion Deodorant | |
|---|---|
| | Parts by Weight |
| DC 245 Fluid | 66.5 |
| DC 225 Fluid | 6.0 |
| Diisopropyl Adipate | 2.0 |
| Hydrogenated castor oil | 1.0 |
| Calcium carbonate (extra fine) | 5.0 |
| Gelatin | 12.0 |
| Sodium citrate | 6.0 |
| Benzyl alcohol | 1.0 |
| Fragrance | 0.5 |
| | 100.0 |

After removing the solvent by evaporation, the powdered dry composition absorbed 2.8 grams of water per gram of solids corresponding to 7.0 grams of water per gram of gelatin.

EXAMPLE 5

| Lotion Antiperspirant | |
|---|---|
| | Parts by Weight |
| DC 245 Fluid | 60.0 |
| DC 225 Fluid | 6.0 |
| Diisopropyl Adipate | 2.0 |
| Hydrogenated castor oil | 1.0 |
| Gelatin | 15.0 |
| Rezal 36 GP SUF | 15.0 |
| Benzyl alcohol | 0.5 |
| Fragrance | 0.5 |
| | 100.0 |

After solvent evaporation, the powdered dry solids absorbed 5.5 grams of water per gram of solids, corresponding to 14 grams of water per gram of gelatin.

We claim:

1. A deodorant composition that is applied to the axillae containing from about 1 to about 25% by weight based on the total weight of the composition of a grade of gelatin that is normally tacky in the presence of perspiration and from about 0.2 to about 25% by weight based on the total weight of the composition of an electrolyte having a cation with a valence of at least three in an amount that is at least adequate to raise the sol-gel transition temperature of the gelatin at least by about two degrees centigrade so that the gelatin is no longer tacky in the presence of perspiration and has an increased capacity to absorb perspiration, in combination with a deodorant in an essentially anhydrous vehicle.

2. A deodorant composition according to claim 1 wherein the vehicle is predominantly polydimethylcyclosiloxane.

3. A and deodorant composition in accordance with claim 1 where the electrolyte is an astringent aluminum and/or zirconium salt.

4. A deodorant composition according to claim 1 wherein the composition contains a deodorant which does not inhibit the flow of perspiration.

5. Non-aerosol composition in accordance with claim 1 where gelatin is in the amount of about 5 to about 25% by weight based on the total weight of the composition.

6. A non-aerosol deodorant composition according to claim 1 wherein the composition contains a deodorant that does not inhibit the flow of perspiration.

7. A non-aerosol deodorant composition according to claim 1 wherein the composition contains sufficient astringent aluminum and/or zirconium salts to effectively inhibit perspiration.

8. A non-aerosol composition according to claim 3 wherein the astringent salt is in an amount of 10 to 25% by weight.

9. An aerosol composition in accordance with claim 1, wherein gelatin is in the amount of about 0.2 to about 10% by weight based on the total weight of the composition.

10. An aerosol according to claim 3 wherein the astringent salt is in an amount of 2 to 5% by weight.

* * * * *

UNITED STATES PATENT AND TRADEMARK OFFICE
CERTIFICATE OF CORRECTION

PATENT NO. : 5,433,943
DATED : July 18, 1995
INVENTOR(S) : Osipow et al.

It is certified that error appears in the above-indentified patent and that said Letters Patent is hereby corrected as shown below:

Column 7, line 21, of Claim 3, delete "and".

Signed and Sealed this

Thirty-first Day of October 1995

Attest:

BRUCE LEHMAN

*Attesting Officer*     *Commissioner of Patents and Trademarks*